United States Patent [19]

Cotton et al.

[11] Patent Number: 4,474,767
[45] Date of Patent: Oct. 2, 1984

[54] PEPTIDE AND PSEUDOPEPTIDE DERIVATIVES

[75] Inventors: Ronald Cotton; Michael B. Giles, both of Congleton; David Timms, Macclesfield, all of England

[73] Assignee: Imperial Chemical Industries PLC, London, England

[21] Appl. No.: 523,773

[22] Filed: Aug. 16, 1983

[30] Foreign Application Priority Data

Oct. 18, 1982 [GB] United Kingdom ................. 8229723

[51] Int. Cl.³ ..................... A61K 37/00; C07C 103/52
[52] U.S. Cl. ............................. 424/177; 260/112.5 E
[58] Field of Search .................. 260/112.5 E; 424/177

[56] References Cited

U.S. PATENT DOCUMENTS

| | | | |
|---|---|---|---|
| 4,221,682 | 9/1980 | Sarantakis | 260/112.5 E |
| 4,320,051 | 3/1982 | Sarantakis | 260/112.5 E |
| 4,322,342 | 3/1982 | Smithwick, Jr. et al. | 260/112.5 E |
| 4,331,593 | 5/1982 | Smithwick, Jr. et al. | 260/112.5 E |

OTHER PUBLICATIONS

Shaw et al., Life Sciences, 1982, 31, 1259–1262 (Pergamon Press).
Gormley et al., Life Sciences, 1982, 31, 1263–1266.
Nagaraj et al., FEBS Letters, 1979, 106, No. 2, 271–274.
Belton et al., Life Sciences, 1983, 33, Suppl. I, 443–446.

*Primary Examiner*—Delbert R. Phillips
*Attorney, Agent, or Firm*—Cushman, Darby & Cushman

[57] ABSTRACT

Compounds of the formula:

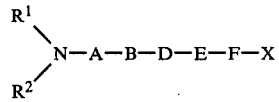

wherein $R^1$ stands for an alk-2-enyl radical of not more than 5 carbon atoms or a furylmethyl radical, $R^2$ stands for an alk-2-enyl or alkyl radical of not more than 5 carbon atoms or a furylmethyl radical, $>N$—A, B, D, E and F stand for defined amino acid or aza-amino-acid residues, and in particular one or both of B and D stand(s) for an amino acid residue of the formula —NH.C(1-3C alkyl)(1-3C alkyl).CO— or a similar residue, and X stands for —$OR^7$ or —$NR^7R^8$, wherein $R^7$ and $R^8$, which may be the same or different, stand for hydrogen or a (1-4C)alkyl radical, and wherein the linkages are all conventional peptide linkages or in the case of D-E the peptide linkage is replaced by the group —$CH_2S$—, and pharmaceutically-acceptable salts thereof. Processes for the manufacture of the compounds. Pharmaceutical compositions comprising one of the compounds and a pharmaceutically-acceptable diluent or carrier. The compounds are selective opiate δ-receptor antagonists.

7 Claims, No Drawings

PEPTIDE AND PSEUDOPEPTIDE DERIVATIVES

This invention relates to peptide and pseudopeptide derivatives which are active as antagonists at opiate receptors in warm-blooded animals.

It is generally recognised that in warm-blooded animals there are at least two distinct types of opiate receptor, i.e. the μ-receptor and the δ-receptor (see Robson & Kosterlitz, Proc. R. Soc. London (B), 1979, 205, 425–432, Goodman et al., Proc. Natl. Acad. Sci. U.S.A., 1980, 77, 6239–6243, and Simon, Trends in Pharmacol. Sci., 1981, 2, 155). Compounds are known, for example naloxone, which are antagonists of natural endogenous agonists, for example enkephalins, at opiate receptors. Most of these known antagonists are more potent at the μ-receptors than at the δ-receptors; that is, they are selective μ-receptor antagonists. Recently, however, there have been described the following two compounds which are selective δ-receptor antagonists:
N,N-diallyl-Tyr-Gly-Gly-Phe-Leu-OCH$_3$
N,N-diallyl-Tyr-Gly-Gly-ψ(CH$_2$S)-Phe-Leu-OH
(Shaw et al., Life Sciences, 1982, 31, 1259–1262, and Gormley et al. ibid, 1263–1266).

Enkephalin derivatives containing one or two Aib residue(s), for example
H-Tyr-Aib-Aib-Phe-Met-NH$_2$ and
H-Tyr-Gly-Aib-Phe-Met-NH$_2$, have been described, and they have been reported to be opiate-type agonists (Nagaraj et al., FEBS Lett., 1979, 106, No. 2, 271–274).

The compounds of the present invention are novel compounds containing one or two Aib, or similar, residue(s) which are selective δ-receptor antagonists.

According to the invention there are provided compounds of the formula:

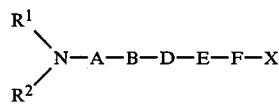
      I wherein:
R$^1$ stands for an alk-2-enyl radical of not more than 5 carbon atoms, or a furylmethyl radical;
R$^2$ stands for an alk-2-enyl or alkyl radical of not more than 5 carbon atoms, or a furylmethyl radical;
>N-A- stands for the residue of D-, L-, D,L- or azatyrosine or -phenylalanine, or a said tyrosine or azatyrosine residue in which the p-hydroxy radical is replaced by a p-t-butoxy substituent or a p-alkanoyloxy or p-alkanoyloxymethoxy substituent of not more than 6 carbon atoms;
B stands for a group of the formula —NH.CR$^3$R$^4$.CO— wherein R$^3$ and R$^4$, which may be the same or different, stand for an n-alkyl radical of not more than 3 carbon atoms, or R$^3$ and R$^4$ are joined to form a polymethylene radical of the formula —(CH$_2$)$_n$— wherein n stands for 2,3,4 or 5, or R$^3$ and R$^4$ are joined to form an alkylene radical of the formula:

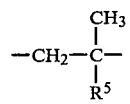
      II wherein
R$^5$ stands for hydrogen or a methyl radical;
D stands for a group of the formula —NH.CR$^3$R$^4$.CO— wherein R$^3$ and R$^4$ have the meanings stated above;
or
one of B and D stands for Gly, Azgly, D-, L- or D,L-Ala or Azala and the other of B and D stands for a group of the formula —NH.CR$^3$R$^4$.CO— wherein R$^3$ and R$^4$ have the meanings stated above;
E stands for the residue of D-, L- or D,L-phenylalanine or -α-methylphenylalanine, or Azphe;
or
E stands for a group of the formula —NHR$^6$ (i.e. the compound is an amide), wherein R$^6$ stands for a 2-phenylethyl, 1-methyl-2-phenylethyl or 1,1-dimethyl-2-phenylethyl radical, or for the group of the formula:

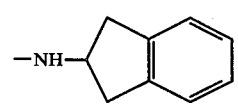
      III or

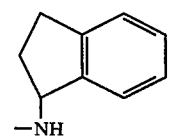
      IV and
F and X are absent;
F stands for the residue of D-, L-, D,L- or azaleucine, methionine or proline; and
X stands for a group of the formula —OR$^7$ (i.e. the compound is a carboxylic acid or an ester) or —NR$^7$R$^8$ (i.e. the compound is an amide), wherein R$^7$ and R$^8$, which may be the same or different, stand for hydrogen or an alkyl radical of not more than 4 carbon atoms;
and wherein the linkages are all conventional peptide linkages (—CO.NH—) or in the case of D-E the peptide linkage is replaced by the group —CH$_2$S—;
and pharmaceutically-acceptable salts thereof.

It is to be understood that the compounds of this invention are characterised by the fact that the groups R$^1$ and R$^2$ are linked to the nitrogen atom of the α-amino group in the residue represented by >N-A-. It is further to be understood that throughout this specification the standard abbreviations for amino acids are used (see Pure and Applied Chemistry, 1974, 40, 317–331, and Neuropeptides, 1981, 1, 231–235). However, for the avoidance of doubt, in this specification the following abbreviations have the meanings indicated:

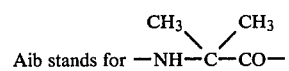
      V

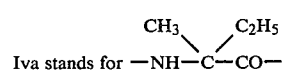
      VI

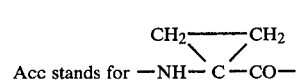
      VII

-continued

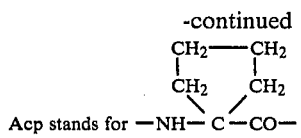

Acp stands for —NH—C—CO—   VIII

An α-aza-amino-acid is one in which the α—CH part of the amino acid has been replaced by a nitrogen atom. The abbreviation for an α-aza-amino-acid is derived from that for the corresponding amino acid by adding the prefix "Az". Thus, for example, Azala stands for α-aza-alanine, Azgly stands for azaglycine, and so on. When the configuration of an amino acid is not designated herein, it is to be understood that it has the natural L-configuration (except, of course, for acids having no chiral centre). In this specification the word "pseudo" has the meaning that, in the compound in question, the conventional peptide linkage between D and E has been replaced by the group —CH$_2$S—. The change from the peptide linkage is indicated by the use of the Greek symbol ψ(psi); see Neuropeptides, 1981, 1, 231–235. It is to be understood that in the compounds of this invention any particular chiral centre may be in the D-, L- or D,L-configuration unless otherwise indicated.

R$^1$ may, for example, stand for an allyl, crotonyl, 2-furylmethyl or 3-furylmethyl radical.

R$^2$ may, for example, stand for an allyl, crotonyl, ethyl, n-propyl, n-butyl, 2-furylmethyl or 3-furylmethyl radical.

When >N-A stands for a tyrosine or azatyrosine residue in which the p-hydroxy radical is replaced by a p-alkanoyloxy or p-alkanoyloxymethoxy substituent of not more than 6 carbon atoms, that substituent may, for example, be an acetoxy, pivaloyloxy or pivaloyloxymethoxy substituent.

R$^3$ and R$^4$ may, for example, stand for a methyl or ethyl radical, or they may be joined to form a dimethylene, trimethylene or tetramethylene radical.

E may, for example, stand for Phe, D-Phe, Azphe, MePhe, or D,L-α-MePhe. Alternatively, in the case where F and X are absent, E may, for example, stand for a group of the formula —NHR$^6$, wherein R$^6$ stands for a 2-phenylethyl radical or a group of the formula III or IV.

F may, for example, stand for Leu, D-Leu, D,L-Leu, Met, D-Met, D,L-Met or Pro.

R$^7$ or R$^8$ may, for example, stand for hydrogen or a methyl or ethyl radical.

A preferred group of compounds of the invention comprises those compounds in which both B and D, which may be the same or different, stand for a group of the formula —NH.CR$^3$R$^4$.CO— wherein R$^3$ and R$^4$ have the meanings stated above.

Preferred compounds of the invention are N,N-diallyl-Tyr-Aib-Aib-Phe-Leu-OH, N,N-diallyl-Tyr-Aib-Aib-Phe-Leu-OCH$_3$ and N,N-diallyl-Tyr-Aib-Acc-Phe-Leu-OCH$_3$, and pharmaceutically-acceptable salts thereof.

The salts of the invention may, in the case where the compound of the formula I is sufficiently basic, be pharmaceutically-acceptable acid-addition salts or, in the case where the said compound is sufficiently acidic, pharmaceutically-acceptable base-addition salts or an aluminium salt. The said acid-addition salts are derived from an inorganic or organic acid which affords a pharmaceutically-acceptable anion, for example hydrochloric, phosphoric, acetic, citric or trifluoroacetic acid. The said base-addition salts are derived from a base which affords a pharmaceutically-acceptable cation, for example ammonia, N-methyl-D-glucosamine or arginine, or they may, for example, be alkali metal salts, for example a sodium or potassium salt.

According to a further feature of the invention there is provided a process for the manufacture of those of the compounds of the formula I wherein R$^1$, R$^2$, A, B, D, E and F have the meanings stated above and X stands for a group of the formula —OR$^9$ or —NR$^7$R$^8$ wherein R$^9$ stands for an alkyl radical of not more than 4 carbon atoms and R$^7$ and R$^8$ have the meanings stated above, and pharmaceutically-acceptable salts thereof, which comprises coupling an amino acid derivative of the formula:

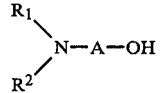   IX wherein R$^1$, R$^2$ and A have the meanings stated above, with a compound of the formula:

   X wherein B, D, E and F have the meanings stated above, and X has the meaning stated immediately above, or a salt thereof.

This coupling reaction can be carried out by methods which are routine in peptide synthesis. For example, the process is conveniently carried out in the presence of dicyclohexylcarbodiimide, which activates the carboxy function in the reactant of the formula IX, and also in the presence of 1-hydroxybenzotriazole, which suppresses undesirable side reactions. The process is conveniently carried out in a suitable organic solvent, for example dimethylformamide. A suitable salt of the compound of the formula X for use in the process is, for example, the hydrochloride. When such a salt is used as a reactant, an organic base, for example a trialkylamine of not more than 9 carbon atoms, for example triethylamine, is conveniently used in the process.

According to a further feature of the invention there is provided a process for the maufacture of compounds of the formula I, wherein R$^1$, R$^2$, A, B, D, E, F and X have the meanings stated above with the exception that >N-A- does not stand for a D-, L-, D,L- or aza-tyrosine residue in which the p-hydroxy radical is replaced by a p-t-butoxy substituent, and pharmaceutically-acceptable salts thereof, which comprises removing one or more conventional protecting groups from a corresponding protected compound by conventional means.

In the case where >N-A stands for a D-, L-, D,L- or aza-tyrosine residue, the protecting group may be a t-butyl radical which may be removed by treatment of the protected derivative with hydrogen chloride or trifluoroacetic acid. Hydrogen chloride may be used in the form of an aqueous solution, at a concentration between 1M and that of a saturated solution, or it may be used as a solution in an organic solvent, for example ethyl acetate, at a concentration in the range 2M to 6M. The process is preferably carried out at a temperature between 0° C. and ambient temperature, and optionally in the presence of a scavenger compound, for example anisole, thioanisole, methionine or dimethyl sulphide. Trifluoroacetic acid may be used as a de-protecting agent by itself or it may be diluted with 5–10% by volume of water. The process involving trifluoroacetic acid is preferably carried out at ambient temperature, and optionally in the presence of a scavenger compound, for example 2-mercaptoethanol or anisole.

According to a further feature of the invention there is provided a process for the manufacture of those of the compounds of the formula I wherein X stands for a hydroxy radical and $R^1$, $R^2$, A, B, D, E and F have the meanings stated above, and pharmaceutically-acceptable salts thereof, which comprises hydrolysing a corresponding (1-6C)alkyl or benzyl ester under alkaline conditions.

A suitable ester is a methyl, ethyl or benzyl ester. A suitable hydrolytic agent is an alkali metal hydroxide, for example sodium hydroxide. The hydrolysis is carried out in the presence of water, and preferably in the presence of methanol or ethanol. The hydrolysis is conveniently carried out at ambient temperature.

According to a further feature of the invention there is provided a process for the manufacture of those of the compounds of the formula I wherein >N-A stands for a D-, L-, D,L- or aza-tyrosine residue in which the p-hydroxy radical is replaced by a p-alkanoyloxy substituent of not more than 6 carbon atoms, and $R^1$, $R^2$, B, D, E, F and X have the meanings stated above, and pharmaceutically-acceptable salts thereof, which comprises acylating a corresponding compound in which >N-A stands for a D-, L-, D,L- or aza-tyrosine residue with an acid halide or an anhydride derived from an alkanoic acid of not more than 6 carbon atoms.

The acid halide may, for example, be an acid chloride, for example acetyl chloride or pivaloyl chloride, and an acid-binding agent, for example an organic base, for example a trialkylamine of not more than 9 carbon atoms, for example triethylamine, may optionally be present in the reaction mixture. The acylation is conveniently carried out in a suitable organic solvent, for example methylene chloride.

According to a further feature of the invention there is provided a process for the manufacture of those of the compounds of the formula I wherein >N-A stands for a D-, L-, D,L- or aza-tyrosine residue in which the p-hydroxy radical is replaced by a p-alkanoyloxymethoxy substituent of not more than 6 carbon atoms, and $R^1$, $R^2$, B, D, E, F and X have the meanings stated above, and pharmaceutically-acceptable salts thereof, which comprises reacting a corresponding compound in which >N-A stands for a D-, L-, D,L- or aza-tyrosine residue with an alkanoyloxymethyl halide of not more than 6 carbon atoms and an acid-binding agent.

A suitable alkanoyloxymethyl halide is, for example, an iodide, for example pivaloyloxymethyl iodide. A suitable acid-binding agent is, for example, an alkali metal carbonate, for example potassium carbonate. The process is conveniently carried out in a suitable organic solvent, for example a dialkyl ketone of not more than 7 carbon atoms, for example acetone.

The compounds used as starting materials in the processes of this invention can be obtained by methods which are routine in peptide synthesis, as is illustrated hereinafter in the Examples and the reaction diagrams. Similarly, the salts of the invention are obtainable by conventional procedures.

The activity of the compounds of the invention as antagonists at opiate receptors has been demonstrated in the guinea pig ileum test ("ileum test") and the mouse vas deferens test ("vas test"); see the article by Shaw et al. in "Characteristics and Functions of Opioids" edited by Van Ree and Terenius, Elsevier/North-Holland Biomedical Press, 1978, 185–195. It is generally recognised that in the guinea pig ileum the $\mu$-receptor predominates, and that in the mouse vas deferens the $\delta$-receptor predominates. The potency of a compound in the above-mentioned tests is expressed as a Ke value, i.e. the concentration of the compound (antagonist) in the presence of which the agonist concentration has to be doubled in order to maintain a constant response. [Leu]-enkephalin is used as the agonist in both tests. The potency of any particular compound in the test depends upon its precise chemical structure, but the compounds of the invention are active in the ileum test at a concentration in the range 100 nM to 30 $\mu$M, and in the vas test at a concentration in the range 1 nM to 10 $\mu$M ($\mu$M stands for micromolar, i.e. $10^{-6}$ mole per liter, and nM stands for nanomolar, i.e. $10^{-9}$ mole per liter).

As an indication of the lack of toxicity of compounds of the invention, it is observed that no toxic effects have been seen with N,N-diallyl-Tyr-Aib-Aib-Phe-Leu-OCH$_3$ (see Example 16) at a subcutaneous dose of 20 mg./kg. in the rat, nor with N,N-diallyl-Tyr-Aib-Aib-Phe-Leu-OH (see Example 19) at a subcutaneous dose of 15 mg./kg. in the rat.

Because of their activity as antagonists at opiate receptors, the compounds of the invention may be used for the treatment of the following conditions and/or diseases in man: schizophrenia and other mental illnesses, stress, shock, stroke (cerebrovascular disorders), anorexia nervosa, epilepsy, disorders of the endocrine function including post-menopausal flushing, and gastro-intestinal disorders. The compounds may also be used as sedatives. When a compound of the invention is used for the treatment of man, it may be administered orally, or parenterally, for example by intravenous, subcutaneous or intramuscular injection or by infusion, or nasally, sub-lingually or rectally. A recommended daily oral dose for man is in the range 1 mg. to 1.0 g. Such a dose may be administered as a single daily dose or it may be divided into, for example, three doses per day. A recommended parenteral dose for man is 1 mg. to 500 mg., a recommended nasal dose is 0.1 mg. to 25 mg., a recommended sub-lingual dose is 1 mg. to 250 mg., and a recommended rectal dose is 2 mg. to 1.0 g.

The compounds of the invention may also be used as research tools or diagnostic agents in pharmacological or other studies.

According to a further feature of the invention there are provided pharmaceutical compositions comprising a compound of the formula I, wherein $R^1$, $R^2$, A, B, D, E, F and X have the meanings stated above, or a pharmaceutically-acceptable salt thereof, and a pharmaceutically-acceptable diluent or carrier.

The pharmaceutical compositions of the invention may be in a form suitable for oral, parenteral, nasal, sub-lingual or rectal administration. Thus, for example, they may be in an orally-administrable unit dosage form, for example tablets or capsules, which may optionally be adapted for sustained or controlled release, or they may be in an injectable form, for example a sterile injectable solution or suspension, or in the form of a nasal spray or a suppository. The pharmaceutical compositions of the invention are obtainable in conventional manner using conventional diluents or carriers.

The pharmaceutical compositions of the invention may optionally contain, in addition to a compound of the invention:

(1) a known opiate antagonist, for example naloxone;

(2) a known psychotropic agent, for example an antipsychotic agent, for example chlorpromazine, or an antidepressant agent, for example imipramine, or an anxiolytic agent, for example chlordiazepoxide;

(3) a known analgesic agent, for example morphine; or (4) a known anticonvulsant agent, for example primidone.

The invention is illustrated but not limited by the following Examples, in which the temperatures are expressed in degrees Celsius, the expression "in vacuo" indicates a pressure of approximately 15 mm.Hg, and the $R_f$ values refer to ascending thin layer chromatgraphy on silica gel (Kieselgel G) plates. The solvent systems used, unless otherwise stated, were as follows (the ratios are by volume):

$R_fK_{NH_3}$ chloroform/methanol/ammonium hydroxide (S.G. 0.880) (60:30:5)

$R_fP$ chloroform/methanol (19:1)

$R_fQ$ chloroform/methanol (9:1)

$R_fQ_{HOAc}$ chloroform/methanol (9:1) containing 1% v/v acetic acid $R_fR_{NH_3}$ chloroform/methanol/ammonium hydroxide (S.G. 0.880) (16:4:1)

The following abbreviations are used in the Examples:

Ac acetyl
Boc t-butoxycarbonyl
Bu$^t$ t-butyl
DCCI dicyclohexylcarbodiimide
DMF dimethylformamide
Me methyl
MS mass spectrum
ODt 3,4-dihydro-4-oxo-1,2,3-benzotriazine-3-oxy-
Ph phenyl
Piv pivaloyl
POM pivaloyloxymethyl
t.l.c. thin layer chromatography The petroleum ether which was used had b.p. 60°–80°.

EXAMPLE 1

N,N-Diallyl-Tyr(Bu$^t$)-OH (1.77 g.), 1-hydroxybenzotriazole (1.51 g.) and H-Aib-Aib-Phe-Leu-OMe (2.35 g.) were dissolved in DMF (15 ml.) and the solution was cooled to 0°. A solution of DCCI (1.15 g.) in DMF (5 ml.) was added and the mixture was stirred at 0° for 2 hr. and then at ambient temperature for 18 hr. The mixture was filtered, the solid residue was washed with DMF (3×5 ml.), and the combined filtrate and washings were evaporated in vacuo. The residue was shaken together with a mixture of ethyl acetate (40 ml.) and 0.5M-potassium carbonate (25 ml.). The mixture was separated and the organic phase was washed successively with 0.5M-potassium carbonate (25 ml.), water (25 ml.), M-sodium dihydrogen phosphate (2×25 ml.), water (25 ml.) and saturated brine (25 ml.), and then dried (MgSO$_4$). The solvent was evaporated in vacuo and the residue was purified by medium pressure liquid chromatography on silica gel (Merck Kieselgel 9385, column 30×3.8 cm., chloroform) to give N,N-diallyl-Tyr(Bu$^t$)-Aib-Aib-Phe-Leu-OMe, M.S: (M+H)$^+$762, $R_fP$ 0.36, $R_fQ$ 0.5, $R_f$ 0.25 (in 50% v/v ethyl acetate/chloroform).

The Aib-containing derivative used as a starting material was obtained as follows:

Boc-Aib-OH (8.12 g.), 1-hydroxybenzotriazole (10.8 g.), H-Phe-Leu-OMe hydrochloride (13.15 g.) and triethylamine (5.4 ml.) were added to stirred DMF (120 ml.). The mixture was cooled to −10°. A solution of DCCI (8.24 g.) in DMF (60 ml.) was added and the mixture was stirred for 1 hr. at 0°. and for 64 hr. at ambient temperature. The mixture was then filtered and the solid residue was washed with DMF (3×20 ml.). The combined filtrate and washings were evaporated in vacuo. The residual oil was shaken together with ethyl acetate (250 ml.) and M-citric acid (150 ml.). The mixture was separated and the organic phase was washed successively with M-citric acid (150 ml.), water (150 ml.), 0.5M-potassium carbonate (2×150 ml.), water (2×150 ml.) and saturated brine (150 ml.). The organic solution was dried (MgSO$_4$) and filtered, and the solvent was evaporated in vacuo. The product was purified using medium pressure liquid chromatography on silica gel (Merck Kieselgel 9385; column 30×3.8 cm.; 9:1 v/v ethyl acetate/petroleum ether), and there was thus obtained Boc-Aib-Phe-Leu-OMe having $R_f$ 0.17 (in 45% v/v ethyl acetate/petroleum ether). This was used in the next step without further purification.

Boc-Aib-Phe-Leu-OMe (14.38 g.) was dissolved in ethyl acetate (25 ml.). A solution of 3M-hydrogen chloride in ethyl acetate (33 ml.) was added and the mixture was stirred at ambient temperature for 1 hr., during which time a white crystalline solid separated out. The solid was collected by filtration, washed with ethyl acetate (3×15 ml.) and then dried in vacuo at ambient temperature to give H-Aib-Phe-Leu-OMe hydrochloride, $R_fK_{NH_3}$ 0.89, $R_fR_{NH_3}$ 0.74.

The last-named compound (6.22 g.), 1-hydroxybenzotriazole (4.46 g.) and Boc-Aib-OH (3.35 g.) were dissolved in DMF (50 ml.), and the resulting solution was cooled to 0°. Triethylamine (2.10 ml.) was added, followed by a solution of DCCI (3.40 g.) in DMF (4 ml.). The mixture was stirred at 0° for 1.5 hr. and then at ambient temperature for 96 hr. The mixture was filtered, the solid residue was washed with DMF (3×10 ml.), and the combined filtrate and washings were evaporated in vacuo. The residue was shaken together with a mixture of ethyl acetate (100 ml.) and 0.5M-potassium carbonate (50 ml.). The mixture was separated and the aqueous phase was washed successively with 0.5-potassium carbonate (50 ml.), water (50 ml.), M-citric acid (2×50 ml.), water (3×50 ml.) and saturated brine (50 ml.). The organic solution was dried (MgSO$_4$) and filtered, and the solvent was evaporated in vacuo. The product was further purified by high performance liquid chromatography on silica gel (Waters Associates Prep-Pak 500; 30% v/v ethyl acetate/chloroform) to give an off-white foam. This foam was triturated with diethyl ether (20 ml.), and the mixture was kept at 4° for 18 hr. The resulting solid was collected by filtration and dried in vacuo at ambient temperature, and there was thus obtained Boc-Aib-Aib-Phe-Leu-OMe, m.p. 141°–2°, $R_fP$ 0.30, $R_f$ 0.20 (in 50% v/v ethyl acetate/chloroform).

The last-named compound (3.5 g.) was dissolved in 3M-hydrogen chloride in ethyl acetate (25 ml.) and the solution was kept at ambient temperature for 3 hr. The solvent was then evaporated in vacuo and the residue was shaken together with ethyl acetate (50 ml.) and water (30 ml.). The mixture was separated, both phases being retained, and the organic phase was extracted with water (25 ml.). The combined aqueous phase and aqueous extract were basified with 0.5M-potassium carbonate (20 ml.) and extracted with ethyl acetate (2×30 ml.). The combined extracts were washed successively with water (25 ml.) and saturated brine (25 ml.), and then dried (MgSO$_4$). The solvent was evaporated in vacuo to give a colourless syrupy residue which crystallised spontaneously. The solid was recrystallised from cyclohexane (25 ml.) containing ethyl acetate (3 ml.), and there was thus obtained H-Aib-Aib-Phe-Leu-OMe, R$_f$Q 0.27.

EXAMPLES 2–15

The following compounds were prepared in an essentially similar way to that described in Example 1 for the preparation of N,N-diallyl-Tyr(Bu$^t$)-Aib-Aib-Phe-Leu-OMe:

Example 2. N,N-diallyl-Tyr-Acc-Aib-Phe-Leu-OMe, MS: (M)$^+$677, R$_f$P 0.19.

Example 3. N,N-diallyl-Tyr-Aib-Acc-Phe-Leu-OMe, MS: (M+H)$^+$704, R$_f$P 0.19, R$_f$Q 0.41.

Example 4. N,N-diallyl-Tyr-D,L-Iva-Aib-Phe-Leu-OMe, MS: (M)$^+$719, R$_f$0.34, 0.31 (t.l.c. on silica gel; ethyl acetate/chloroform 8:1 v/v).

Example 5. N,N-diallyl-Tyr-Aib-D,L-Iva-Phe-Leu-OMe, MS: (M+H)$^+$720, R$_f$0.11 (t.l.c. on silica gel; ethyl acetate/chloroform 1:1 v/v).

Example 6. N,N-diallyl-Tyr-Acp-Aib-Phe-Leu-OMe, MS: (M+H)$^+$732, R$_f$P 0.30, R$_f$Q 0.51.

Example 7. N,N-diallyl-Tyr-Aib-Acp-Phe-Leu-OMe, MS: (M+H)$^+$732, R$_f$Q 0.46.

Example 8. N,N-diallyl-Tyr-Ala-Aib-Phe-Leu-OMe, MS: (M+H)$^+$692, R$_f$Q 0.29.

Example 9. N,N-diallyl-Tyr-Aib-Ala-Phe-Leu-OMe, MS: (M+H)$^+$692, R$_f$Q 0.18.

Example 10. N,N-diallyl-Tyr-D-Ala-Aib-Phe-Leu-OMe, MS: (M+H)$^+$692, R$_f$Q 0.23.

Example 11. N,N-diallyl-Tyr-Aib-D-Ala-Phe-Leu-OMe, MS: (M+H)$^+$692, R$_f$Q 0.24.

Example 12. N-allyl-N-n-propyl-Tyr-Aib-Aib-Phe-Leu-OMe, MS: (M+H)$^+$708, R$_f$Q 0.61.

Example 13. N-2-furylmethyl-N-n-propyl-Tyr-Aib-Aib-Phe-Leu-OMe, MS: (M+H)$^+$748, R$_f$Q 0.35.

Example 14. N,N-diallyl-Phe-Aib-Aib-Phe-Leu-OMe, MS: (M+H)$^+$690, R$_f$P 0.54.

Example 15. N,N-diallyl-Tyr-Aib-Aib-NH(CH$_2$)$_2$Ph, MS: (M+H)$^+$535, R$_f$P 0.22.

The conventional methods used to prepare the starting materials used in the above Examples are outlined in the following reaction diagrams [each diagram has at least one number preceded by the letter D; the number(s) indicate(s) the corresponding Example(s)]:

D2

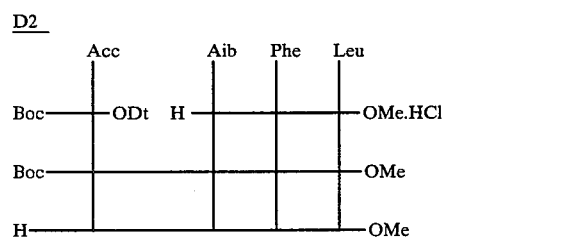

D3

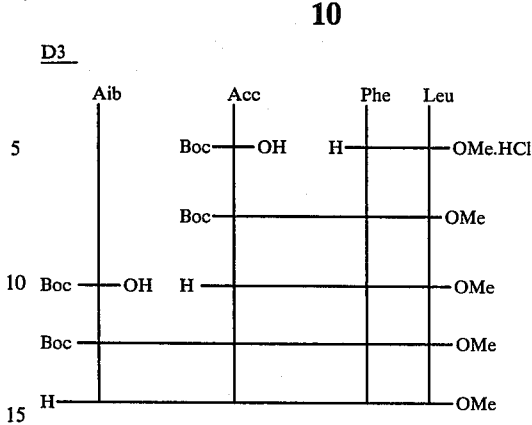

D4

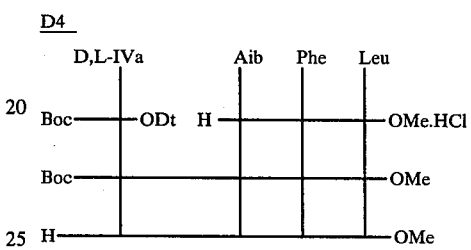

D5

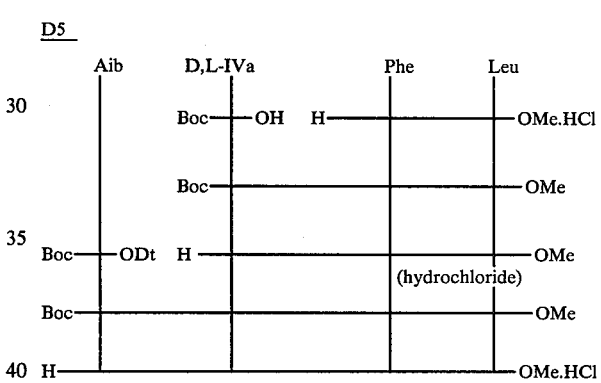

D6

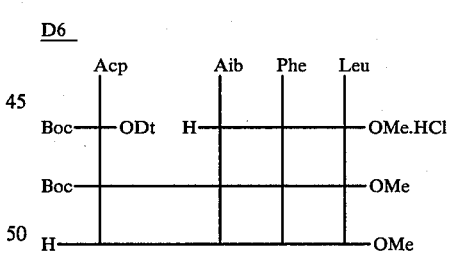

D7

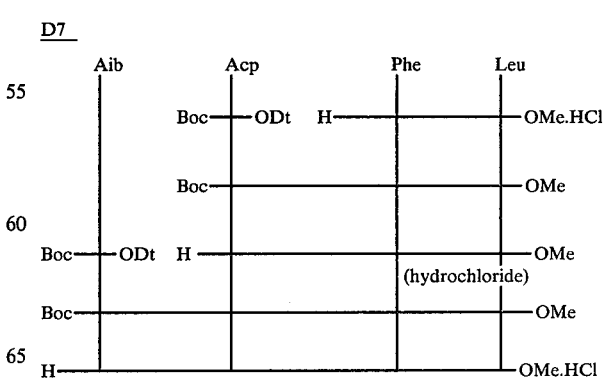

D8
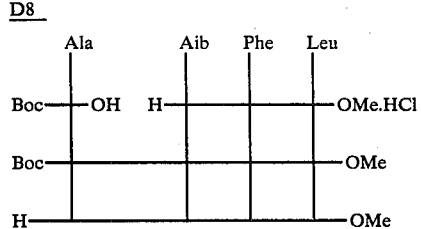

D9
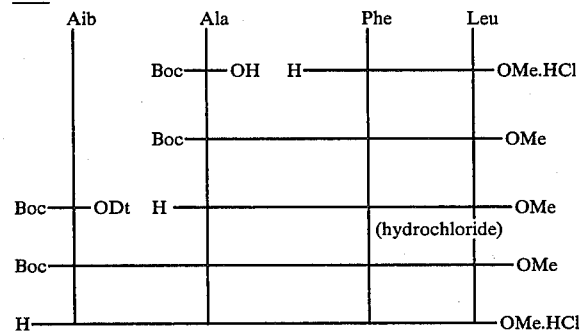

D10
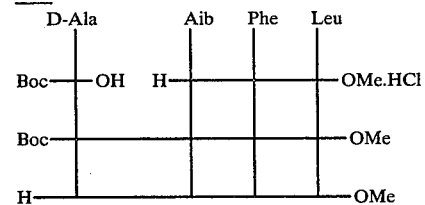

D11
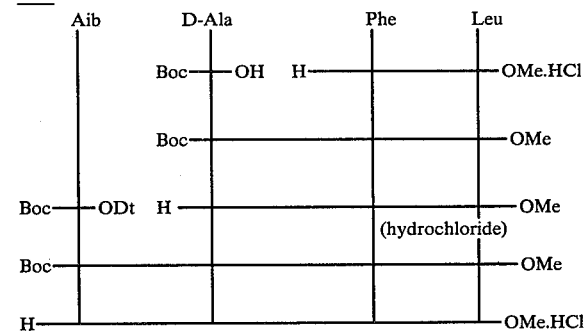

EXAMPLE 16

N,N-Diallyl-Tyr(Bu$^t$)-Aib-Aib-Phe-Leu-OMe (2.4 g; see Example 1) was dissolved in ethyl acetate (5 ml.). To the solution was added a 3M-solution of hydrogen chloride in ethyl acetate (5 ml.), and the mixture was kept at ambient temperature for 2 hr. The solvent was then evaporated in vacuo and the residue was shaken with a mixture of ethyl acetate (25 ml.) and 0.5M-potassium carbonate solution (15 ml.). The mixture was separated and the organic phase was washed successively with 0.5M-potassium carbonate solution (15 ml.), water (2×15 ml.) and saturated brine (15 ml.), and then dried (MgSO$_4$). The solvent was evaporated in vacuo and the product was purified by chromatography on silica gel (Merck Kieselgel 7754, column 15×1.1 cm., elution with 0-5% v/v methanol/chloroform). The appropriate fractions (detected by thin layer chromatography) were combined and the solvent evaporated in vacuo. The residue was freeze-dried from 95% v/v t-butanol/water, and there was thus obtained N,N-diallyl-Tyr-Aib-Aib-Phe-Leu-OMe, MS: (M+H)$^+$706, R$_f$Q 0.40, and R$_f$ 0.12 (tlc on silica gel; 50% v/v ethyl acetate/chloroform).

EXAMPLES 17 AND 18

The following compounds were prepared in an essentially similar way to that described in Example 16:

Example 17. N,N-diallyl-Tyr-Gly-Aib-Phe-Leu-OMe, MS: (M-C$_3$H$_5$)$^+$636, R$_f$Q 0.37.

Example 18. N,N-diallyl-Tyr-Aib-Gly-Phe-Leu-OMe, MS: (M)$^{.+}$677, R$_f$Q 0.48.

The conventional methods used to prepare the starting materials used in these Examples are outlined in the following reaction diagrams:

D17
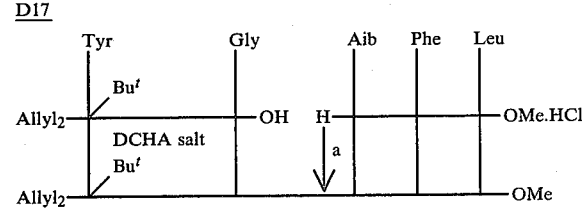

DCHA = dicyclohexylamine;
a DMF, (CH$_3$)$_3$C.COCl, Et$_3$N

D18

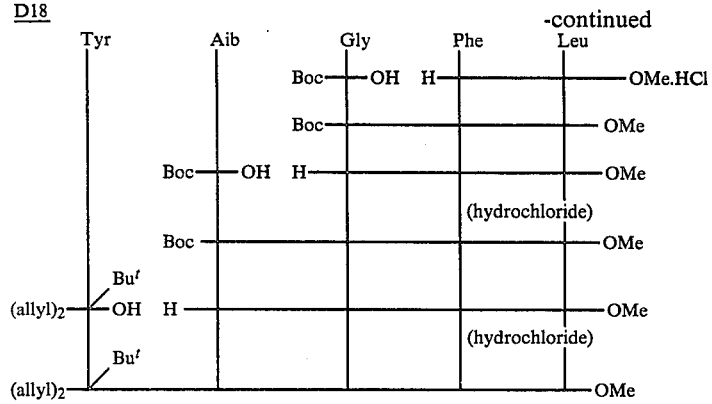

EXAMPLE 19

N,N-Diallyl-Tyr-Aib-Aib-Phe-Leu-OMe (1.25 g.; see Example 16) was dissolved in methanol (10 ml.). A solution of 2M-sodium hydroxide (1.95 ml.) was added and the mixture was stirred for 3 hr. at 20° and then for 18 hr. at 5°. The solvent was evaporated in vacuo and the residue was shaken together with a mixture of water (30 ml.) and ethyl acetate (10 ml.). The two phases were separated, and the aqueous phase was washed with ethyl acetate (10 ml.). The aqueous phase was freed from residual ethyl acetate by partial evaporation in vacuo, and then diluted to 50 ml. with methanol. The solution was applied to a column (20 ml.) of a weakly acidic cation-exchange resin (Biorex 70, hydrogen form), and eluted with 50% v/v aqueous methanol. The eluate was evaporated in vacuo to dryness and the residue was freeze-dried from 95% v/v t-butanol/water to give N,N-diallyl-Tyr-Aib-Aib-Phe-Leu-OH, MS: (M)·+691, $R_f Q_{HOAc}$ 0.19.

EXAMPLE 20

N,N-Diallyl-Tyr-Aib-Aib-Phe-Leu-OMe (0.50 g.; see Example 16) and triethylamine (0.207 ml.) were dissolved in methylene chloride (5 ml.). The solution was cooled to −10°, pivaloyl chloride (0.105 ml.) was added, and the mixture was stirred for 30 min. at −5° and then for 18 hr. at 20°. The solvent was evaporated in vacuo, and the residue was shaken together with ethyl acetate (20 ml.) and 0.5M-potassium carbonate (10 ml.). The mixture was separated and the organic phase was washed successively with M-sodium dihydrogen phosphate (2×10 ml.) and saturated brine (10 ml.). The organic phase was dried (MgSO₄) and the solvent evaporated in vacuo. The product was further purified by medium-pressure liquid chromatography on silica gel (Merck Kieselgel 9385; 75% v/v ethyl acetate/petroleum ether) to give a colourless oil. This oil was freeze-dried from 95% v/v t-butanol/water to give N,N-diallyl-Tyr(Piv)-Aib-Aib-Phe-Leu-OMe, MS: (M+H)+790, $R_f Q$ 0.38.

EXAMPLE 21

In an essentially similar manner to that described in Example 20, using acetyl chloride as the acylating agent, there was obtained N,N-diallyl-Tyr(Ac)-Aib-Aib-Phe-Leu-OMe, MS: (M+H)+748, $R_f P$ 0.43, $R_f Q$ 0.57.

EXAMPLE 22

A mixture of N,N-diallyl-Tyr-Aib-Aib-Phe-Leu-OMe (0.50 g.; see Example 16), anhydrous potassium carbonate (0.14 g.) and pivaloyloxymethyl iodide (0.24 g.) in acetone (5 ml.) was stirred for 18 hr. at 20°. The mixture was filtered and the solvent was evaporated from the filtrate in vacuo. The residue was shaken together with ethyl acetate (30 ml.) and water (10 ml.). The two phases were separated, both being retained. The aqueous phase was extracted with ethyl acetate (10 ml.). The two organic phases were combined and washed successively with M-sodium dihydrogen phosphate (2×10 ml.) and saturated brine (10 ml.). The organic solution was dried (MgSO₄) and the solvent evaporated in vacuo, leaving a clear yellow oil as the residue. The product was further purified by medium pressure liquid chromatography (see Example 20 for details) to give a clear colourless oil. This oil was freeze-dried from 95% v/v t-butanol/water to give N,N-diallyl-Tyr(POM)-Aib-Aib-Phe-Leu-OMe, MS: (M-CO and C₄H₈)+719, $R_f Q$ 0.61.

What we claim is:

1. A compound of the formula:

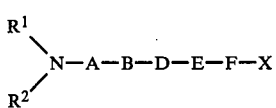

wherein:

R¹ stands for an alk-2-enyl radical of not more than 5 carbon atoms, or a furylmethyl radical;

R² stands for an alk-2-enyl or alkyl radical of not more than 5 carbon atoms, or a furylmethyl radical;

>N-A stands for the residue of D-, L-, D,L- or azatyrosine or -phenylalanine, or a said tyrosine or azatyrosine residue in which the p-hydroxy radical is replaced by a p-t-butoxy substituent or a p-alkanoyloxy or p-alkanoyloxymethoxy substituent of not more than 6 carbon atoms;

B stands for a group of the formula —NH.CR³R⁴.CO— wherein R³ and R⁴, which may be the same or different, stand for an n-alkyl radical of not more than 3 carbon atoms, or R³ and R⁴ are joined to form a polymethylene radical of the formula —(CH₂)ₙ— wherein n stands for 2,3,4 or 5, or R³ and R⁴ are joined to form an alkylene radical of the formula:

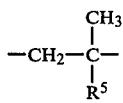                II wherein
R⁵ stands for hydrogen or a methyl radical;
D stands for a group of the formula —NH.CR³R⁴.CO— wherein R³ and R⁴ have the meanings stated above;
or one of B and D stands for Gly, Azgly, D-, L- or D,L-Ala or Azala and the other of B and D stands for a group of the formula —NH.CR³R⁴.CO— wherein R³ and R⁴ have the meanings stated above;
E stands for the residue of D-, L- or D,L-phenylalanine or -α-methylphenylalanine, or Azphe;
or E stands for a group of the formula —NHR⁶, wherein R⁶ stands for a 2-phenylethyl, 1-methyl-2-phenylethyl or 1,1-dimethyl-2-phenylethyl radical, or for the group of the formula:

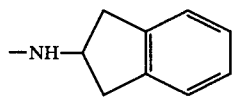                III or

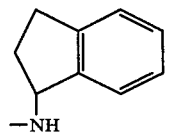                IV and
F and X are absent;
F stands for the residue of D-, L-, D,L- or aza-leucine, methionine or proline; and
X stands for a group of the formula —OR⁷ or —NR⁷R⁸, wherein R⁷ and R⁸, which may be the same or different, stand for hydrogen or an alkyl radical of not more than 4 carbon atoms;
and wherein the linkages are all conventional peptide linkages or in the case of D-E the peptide linkage is replaced by the group —CH₂S—;
or a pharmaceutically-acceptable salt thereof.

2. A compound as claimed in claim 1 of the formula:

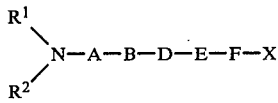                I wherein:
R¹ stands for an alk-2-enyl radical of not more than 5 carbon atoms, or a furylmethyl radical;
R² stands for an alk-2-enyl or alkyl radical of not more than 5 carbon atoms, or a furylmethyl radical;
>N-A stands for the residue of D-, L-, D,L- or azatyrosine or -phenylalanine, or a said tyrosine or azatyrosine residue in which the p-hydroxy radical is replaced by a p-alkanoyloxy or p-alkanoyloxymethoxy substituent of not more than 6 carbon atoms;
B stands for a group of the formula —NH.CR³R⁴.CO— wherein R³ and R⁴ stand for methyl, or R³ and R⁴ are joined to form a polymethylene radical of the formula —(CH₂)ₙ— wherein n stands for 2,3,4 or 5, or R³ and R⁴ are joined to form an alkylene radical of the formula:

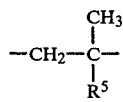                II wherein R⁵ stands for hydrogen or a methyl radical;
D stands for a group of the formula —NH.CR³R⁴.CO— wherein R³ and R⁴ have the meanings stated above;
or one of B and D stands for D-Ala or Azala and the other of B and D stands for a group of the formula —NH.CR³R⁴.CO— wherein R³ and R⁴ have the meanings stated above;
or B stands for Gly or Azgly and D stands for a group of the formula —NH.CR³R⁴.CO— wherein R³ and R⁴ have the meanings stated above;
E stands for the residue of D-, L- or D,L-phenylalanine or -α-methylphenylalanine, or Azphe;
or E stands for a group of the formula —NHR⁶, wherein R⁶ stands for a 2-phenylethyl, 1-methyl-2-phenylethyl or 1,1-dimethyl-2-phenylethyl radical, or for the group of the formula:

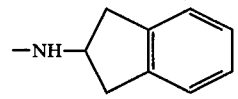                III or

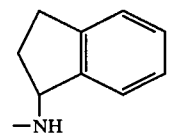                IV and
F and X are absent;
F stands for the residue of D-, L-, D,L - or aza-leucine, methionine or proline; and
X stands for a group of the formula —OR⁷ or —NR⁷R⁸ wherein R⁷ and R⁸, which may be the same or different, stand for hydrogen or an alkyl radical of not more than 4 carbon atoms;
and wherein the linkages are all conventional peptide linkages or in the case of D-E the peptide linkage is replaced by the group —CH₂S—;
or a pharmaceutically-acceptable salt thereof.

3. A compound as claimed in claim 1 or 2 wherein both B and D, which may be the same or different, stand for a group of the formula —NH.CR³R⁴.CO— wherein R³ and R⁴ have the meanings stated in claim 1.

4. A compound as claimed in claim 1 which is N,N-diallyl-Tyr-Aib-Aib-Phe-Leu-OH or a pharmaceutically-acceptable salt thereof.

5. A compound as claimed in claim 2 which is N,N-diallyl-Tyr-Aib-Aib-Phe-Leu-OCH$_3$ or a pharmaceutically-acceptable salt thereof.

6. A compound as claimed in claim 1 which is N,N-diallyl-Tyr-Aib-Acc-Phe-Leu-OCH$_3$ or a pharmaceutically-acceptable salt thereof.

7. A pharmaceutical composition suitable for use as an opiate receptor antagonist comprising an effective amount of a compound of the formula I stated in claim 1, wherein R$^1$, R$^2$, A, B, D, E, F and X have the meanings stated in claim 1, or a pharmaceutically-acceptable salt thereof, and a pharmaceutically-acceptable diluent or carrier.

* * * * *